US012628819B2

(12) United States Patent (10) Patent No.: US 12,628,819 B2
Li et al. (45) Date of Patent: May 19, 2026

(54) VITRIFICATION FREEZING CARRIER

(71) Applicant: SUZHOU BASECARE MEDICAL DEVICE CO., LTD., Jiangsu (CN)

(72) Inventors: Hao Li, Jiangsu (CN); Honghua Shen, Jiangsu (CN); Lei Jiang, Jiangsu (CN); Bo Liang, Jiangsu (CN)

(73) Assignee: SUZHOU BASECARE MEDICAL DEVICE CO., LTD., Suzhou (CN)

( * ) Notice: Subject to any disclaimer, the term of this patent is extended or adjusted under 35 U.S.C. 154(b) by 948 days.

(21) Appl. No.: 17/640,481

(22) PCT Filed: Nov. 26, 2019

(86) PCT No.: PCT/CN2019/121073
§ 371 (c)(1),
(2) Date: Mar. 4, 2022

(87) PCT Pub. No.: WO2021/042587
PCT Pub. Date: Mar. 11, 2021

(65) Prior Publication Data

US 2022/0408721 A1 Dec. 29, 2022

(30) Foreign Application Priority Data

Sep. 6, 2019 (CN) .......................... 201910840190.0

(51) Int. Cl.
*A01N 1/147* (2025.01)
*A61B 10/00* (2006.01)
*B01L 3/00* (2006.01)
(52) U.S. Cl.
CPC .......... *A01N 1/147* (2025.01); *A61B 10/0096* (2013.01); *B01L 3/502* (2013.01);
(Continued)

(58) Field of Classification Search
CPC ..... A01N 1/147; A61B 10/0096; B01L 3/502; B01L 2200/026; B01L 2300/042;
(Continued)

(56) References Cited

U.S. PATENT DOCUMENTS 8,372,633 B2 2/2013 Chairaz et al.
10,531,657 B2 1/2020 Farrington et al.
(Continued)

FOREIGN PATENT DOCUMENTS

CN 101087658 A 12/2007
CN 101200706 A 6/2008
(Continued)

OTHER PUBLICATIONS

Zhang et al., "Comparison of Two Cryopreservation Carriers in Vitrification Cryopreservation of Human Embryo", Journal of Shanghai Jiao Tong University, Medical Science, vol. 34, No. 3, pp. 370-373, Mar. 2014 (English Abstract).
(Continued)

*Primary Examiner* — Charles Capozzi
*Assistant Examiner* — Jacqueline Brazin
(74) *Attorney, Agent, or Firm* — Howson & Howson LLP

(57) ABSTRACT

Provided a vitrification freezing carrier includes a tube body of a hollow structure with an opened end provided with a matching part, a tube cap provided with a covering part of a hollow structure with one end closed and matching the matching part and provided with an extending part connected to the covering part, a carrying rod arranged on a side, facing an interior of the tube body, of the covering part and capable of extending into the tube body, and an auxiliary sampling mechanism including a carrier body provided with a locking part configured to be matched with the covering part to drive the covering part to move and an elastic reset assembly arranged on the carrier body and including a
(Continued)

driving part and an elastic part driven by the driving part and capable of being selectively connected to the extending part in a matched manner.

14 Claims, 8 Drawing Sheets

(52) U.S. Cl.
CPC ... *B01L 2200/026* (2013.01); *B01L 2300/042* (2013.01); *B01L 2300/0832* (2013.01); *B01L 2300/0848* (2013.01); *B01L 2300/123* (2013.01)

(58) Field of Classification Search
CPC ..... B01L 2300/0832; B01L 2300/0848; B01L 2300/123
USPC ........................................................ 435/307.1
See application file for complete search history.

(56) References Cited

U.S. PATENT DOCUMENTS

| | | | |
|---|---|---|---|
| 2008/0038155 A1 | 2/2008 | Chian et al. | |
| 2009/0120106 A1 | 5/2009 | Chin | |
| 2014/0308655 A1 | 10/2014 | Mogas et al. | |
| 2015/0150241 A1* | 6/2015 | Katkov | A01N 1/145 |
| | | | 435/307.1 |
| 2016/0174545 A1 | 6/2016 | Parra et al. | |
| 2016/0363362 A1 | 12/2016 | Chen et al. | |
| 2016/0363363 A1 | 12/2016 | Chen et al. | |
| 2019/0162639 A1 | 5/2019 | Gutelius et al. | |
| 2019/0212318 A1* | 7/2019 | Tang | B01L 5/00 |
| 2020/0093122 A1* | 3/2020 | Lin | A01N 1/147 |

FOREIGN PATENT DOCUMENTS

| | | | |
|---|---|---|---|
| CN | 101272861 A | 9/2008 | |
| CN | 101386814 A | 3/2009 | |
| CN | 201222947 Y | 4/2009 | |
| CN | 201229470 Y | 4/2009 | |
| CN | 201379022 Y | 1/2010 | |
| CN | 101918802 A | 12/2010 | |
| CN | 203340879 U | 12/2013 | |
| CN | 203860325 U | 10/2014 | |
| CN | 203913154 U | 11/2014 | |
| CN | 204047749 U | 12/2014 | |
| CN | 104986426 A | 10/2015 | |
| CN | 104986447 A | 10/2015 | |
| CN | 106489915 A | 3/2017 | |
| CN | 206333261 | * | 7/2017 |
| CN | 206333261 U | 7/2017 | |
| CN | 206713921 U | 12/2017 | |
| CN | 206713922 U | 12/2017 | |
| CN | 206851879 U | 1/2018 | |
| CN | 207305900 U | 5/2018 | |
| CN | 108260587 A | 7/2018 | |
| CN | 108541702 A | 9/2018 | |
| CN | 109362705 A | 2/2019 | |
| CN | 208480533 U | 2/2019 | |
| CN | 109430245 A | 3/2019 | |
| CN | 208798591 U | 4/2019 | |
| CN | 209089795 U | 7/2019 | |
| CN | 209234768 U | 8/2019 | |
| CN | 110476952 A | 11/2019 | |
| FR | 2574919 A1 | 6/1986 | |
| JP | 2015-078147 A | 4/2015 | |
| WO | 2011/144352 A1 | 11/2011 | |
| WO | 2016/016886 A1 | 2/2016 | |
| WO | 2016/100962 A1 | 6/2016 | |
| WO | 2016/158479 A1 | 10/2016 | |
| WO | 2017/099865 A1 | 6/2017 | |

OTHER PUBLICATIONS

Xian et al., "Comparison of The Cryopreservation Effects of Cleavage Stage Embryos with Vitrification in Three Frozen Carriers in Mice", Chinese Journal of Clinical Research, vol. 27, No. 6, pp. 658-660, Jun. 2014 (English Abstract).

Zhang et al., "The Application of Close-Carrier of Vitrification in Human Embryos", Acta Universitatis Medicinalis Anhui, vol. 48, No. 9, pp. 1133-1135, Sep. 2013 (English Abstract).

Shi et al., "Animal Models of Tracheal Allotransplantation using Vitrified Cryopreservation", The Journal of Thoracic and Cardiovascular Surgery, vol. 138, No. 5, pp. 1222-1226, Nov. 2009.

International Search Report of the International Searching Authority issued for International PCT Application No. PCT/CN2019/121073 on Jun. 9, 2020.

European Search Report issued by the European Patent Office for counterpart European Patent Application No. 19944439.9, Sep. 25, 2023.

* cited by examiner

VITRIFICATION FREEZING CARRIER

CROSS-REFERENCE TO RELATED APPLICATION(S)

This is a national stage application filed under 37 U.S.C. 371 based on International Patent Application No. PCT/CN2019/121073, filed Nov. 26, 2019, which claims priority to Chinese Patent Application No. 201910840190.0 filed Sep. 6, 2019, the disclosures of which are incorporated herein by reference in their entireties.

FIELD

This application relates to the technical field of biological sample storage, and in particular to a vitrification freezing carrier.

BACKGROUND

As vitrification freezing technology becomes more and more mature, its applications in biological sample aspects are increasing. The basic principle of the vitrification freezing technology is a process in which the cells is first replaced water therein with a high-concentration cryoprotectant solution, and is then converted from a liquid state to a glass-like amorphous solid state by cooling down rapidly. While cooling down rapidly, since the water in the cells has been replaced, the damage to the lipid membrane and cytoskeleton structure of the cell due to the formation of ice crystals at a low temperature can be avoided to achieve the effect of cryoprotection, thereby improving both the viability of biological samples and developmental ability of the biological samples when resuscitated after frozen. Vitrification freezing technology has the advantages of simplicity, high efficiency, low cost, high survival rate, and the like.

Conventional vitrification freezing carriers mainly include an elongated straw, a cryoloop, a cryotop, and a cryoleaf. The above-mentioned vitrification freezing carriers have sample storage areas relatively fragile and prone to be broken, and the above-mentioned vitrification freezing carriers cannot implement to be grabbed automatically, or cannot implement their caps to be automatically opened and closed.

SUMMARY

Based on this, it is necessary to provide a vitrification freezing carrier to solve the problem that the conventional vitrification freezing carrier cannot implement to be grabbed automatically, or cannot implement their caps to be automatically opened and closed.

A vitrification freezing carrier is provided, which includes a tube body, a tube cap, a carrying rod and an auxiliary sampling mechanism. The tube body is of a hollow structure with an opened end, and a matching part is provided at the opened end. The tube cap is provided with a covering part matching the matching part and is provided with an extending part connected to the covering part.

The covering part is of a hollow structure with one end closed. The carrying rod is arranged on a side, facing an interior of the tube body, of the covering part and the carrying rod is capable of extending into the tube body. The auxiliary sampling mechanism includes a carrier body and an elastic reset assembly arranged on the carrier body. The carrier body is provided with a locking part configured to be matched with the covering part to drive the covering part to move, and the elastic reset assembly includes a driving part and an elastic part driven by the driving part, and the elastic part can be selectively connected to the extending part in a matched manner.

The above technical solutions have at least technical effects as follows. The vitrification freezing carrier according to the present disclosure includes the tube body, the tube cap, the carrying rod and the auxiliary sampling mechanism. By utilizing the assembling relationship among the tube body, the tube cap, the carrying rod and the auxiliary sampling mechanism, the storage of a variety of biological samples can be realized. The auxiliary sampling mechanism can quickly and accurately assist in locking the tube cap to the tube body or in loosening the tube cap from the tube body, to realize sampling and storage. The auxiliary sampling mechanism can also facilitate automatic grabbing the overall structure of the vitrification freezing carrier and reduce mechanical damage to the tube cap and the tube body. Moreover, through the extension of the auxiliary sampling mechanism, the hand when opening or closing the cap may be prevented from being frosted by the liquid nitrogen in which the biological sample is immersed.

In one implementation, the extending part is of a hollow structure with two opened ends, and the extending part and the covering part are in connection and communication with each other in a direction parallel to a center line of the tube body.

In one implementation, a mounting part is provided on the side, facing the interior of the tube body, of the covering part, and the mounting part is assembled with the carrying rod.

In one implementation, the carrier body is provided with an accommodating chamber, and the driving part is partially accommodated in the accommodating chamber and partially exposed to an outside of the carrier body; and the elastic part is accommodated in the accommodating chamber, and is capable of being partially exposed to the outside of the carrier body.

In one implementation, the driving part includes a movable button and a movable body which are connected to each other, the movable button is exposed to an outside of the carrier body, and the movable body is connected to the elastic part and accommodated in the accommodating chamber.

In one implementation, the movable body is provided with a bent part connected to the movable button, and the carrier body is provided with a position-limiting part at the accommodating chamber, and a reset member extending and retracting in a moving direction of the movable body is provided between the bent part and the position-limiting part.

In one implementation, the carrier body is provided with an opening in communication with the accommodating chamber, the elastic part includes a fixed body and a deformable body which are connected to each other, the fixed body is connected to the driving part, and the deformable body is capable of extending out of the opening or be retractable from the opening.

In one implementation, the tube body is provided with a gas discharge passage which allows an inside of the tube body is in communication with an outside of the tube body, the gas discharge passage is embedded in the matching part, the gas discharge passage is provided with an inlet end and an outlet end, the inlet end is arranged on a side, away from the extending part, of the matching part and faces the inside of the tube body, and the outlet end is arranged on a side, close to the extending part, of the matching part and faces the outside of the tube body.

In one implementation, a two-dimensional code is provided on a side of the tube body and/or a bottom of the tube body.

In one implementation, a counterweight is embedded in a bottom of the tube body, and a center line of the counterweight coincides with a center line of the tube body.

In which:

| | | |
|---|---|---|
| 100. Vitrification Freezing Carrier | 110. Tube Body | 112. Matching Part |
| 114. Gas Discharge Passage | 116. Inlet End | 118. Outlet End |
| 119. Position-Limiting Protrusion | 120. Tube Cap | 122. Covering Part |
| 123. Position-Limiting Rib | 124. Mounting Part | 126. Extending Part |
| 128. Knurled Groove | 130. Carrying Rod | 132. Sample placement region |
| 134. Indication region | 136. Identification Mark | 138. Round Hole Mark |
| 140. Auxiliary Sampling Mechanism | 142. Reset Member | 150. Carrier body |
| 152. Locking Part | 154. Accommodating Chamber | 156. Position-Limiting Part |
| 158. Opening | 160. Elastic Reset Assembly | 161. Driving Part |
| 162. Movable Button | 163. Movable Body | 164. Bent Part |
| 165. Elastic Part | 166. Fixed Body | 167. Deformable Body |
| 170. Two-Dimensional Code | 180. Writing Region | 190. Counterweight |
| 129. Sealing Ring | | |

DETAILED DESCRIPTION

In order to make the above-described object, features and advantages of the present disclosure more obvious and understandable, the embodiments of the present disclosure are described in detail hereinafter in conjunction with the drawings. Many specific details are set forth in the description hereinafter to facilitate a thorough understanding of the present disclosure. However, the present disclosure can be implemented in many other ways different from those described herein, and those skilled in the art can make similar improvements without departing from the connotation of the present disclosure. Therefore, the present disclosure is not limited by the embodiments disclosed below.

It is to be noted that when an element is described as being "fixed to" another element, the element may be directly fixed to the other element or may be fixed to the other element via an intermediated element. When an element is described as being "connected to" another element, the element may be directly connected to the other element or may be connected to the other element via an intermediated element.

Unless otherwise defined, all technical and scientific terms used herein have the same meanings as the terms commonly understood by those skilled in the art. The terms used herein in the description of the present disclosure are intended only for the purpose of describing the embodiments, and are not intended to limit the present disclosure. The term "and/or" used herein includes any or all combinations of one or more related listed items.

Figure 1:
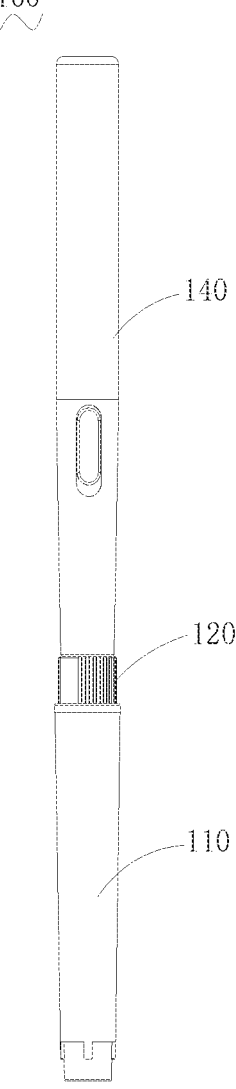
FIG. 1 is a schematic view of an appearance of a vitrification freezing carrier according to an embodiment of the present disclosure.
Figure 2:
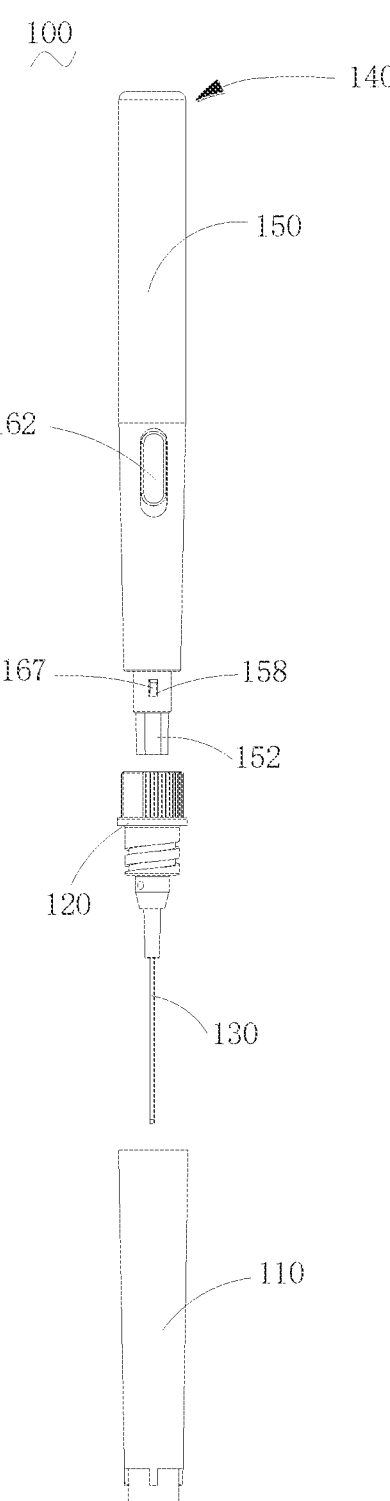
FIG. 2 is a schematic exploded view of the vitrification freezing carrier shown in FIG. 1.
Figure 3:
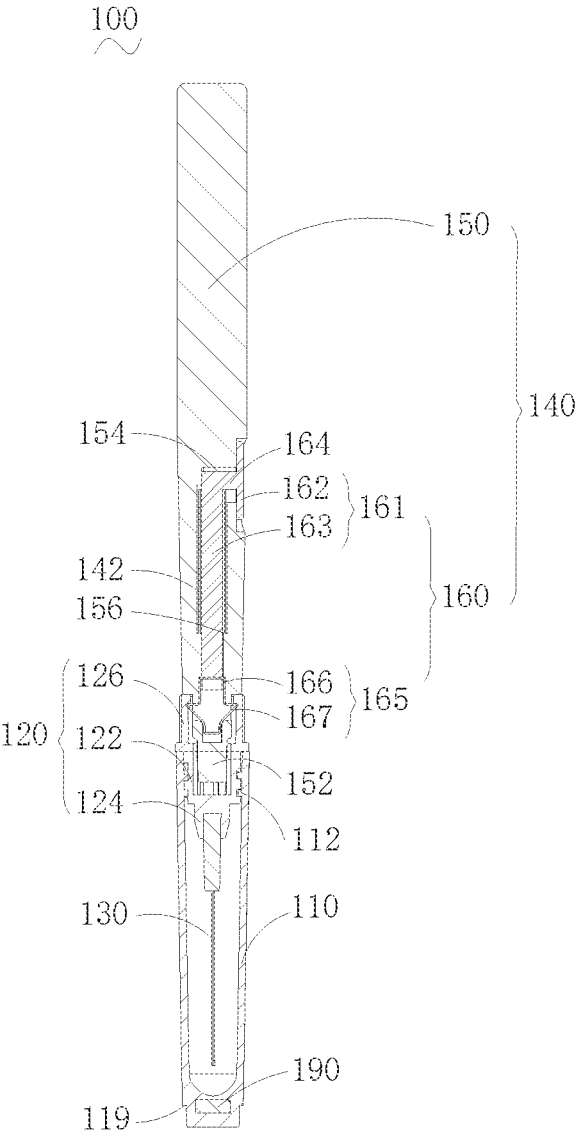
FIG. 3 is a schematic cross-sectional view of the vitrification freezing carrier shown in FIG. 1.

Referring to FIGS. 1 to 3, a vitrification freezing carrier 100 is provided according to an embodiment of the present disclosure, which includes a tube body 110, a tube cap 120, a carrying rod 130 and an auxiliary sampling mechanism 140. The tube body 110 is of a hollow structure with an opened end, and a matching part is provided at the opened end 112. The tube cap 120 is provided with a covering part 122 matching the matching part 112 and an extending part 126 connected to the covering part 122, the covering part 122 is of a hollow structure with one end closed, and the covering part 122 is configured to close the opened end. The carrying rod 130 is arranged on a side, facing the interior of the tube body 110, of the covering part 122 and the carrying rod 130 is capable of extending into the tube body 110. The auxiliary sampling mechanism 140 includes a carrier body 150 and an elastic reset assembly 160 arranged on the carrier body 150. The carrier body 150 is provided with a locking part 152 configured to be matched with the covering part 122 to drive the covering part 122 to move. The elastic reset assembly 160 includes a driving part 161 and an elastic part 165 driven by the driving part 161, and the elastic part 165 can be selectively connected to the extending part 126 in a matched manner.

In some embodiments, the tube body 110 is of a hollow structure with an opened end and with a certain wall thickness, and the matching part 112 is provided near the opened end. The tube cap 120 is provided with the covering part 122 and the extending part 126, and one end of the covering part 122 is closed to achieve sealing of the tube cap 120 to the tube body 110.

An outer wall of the extending part 126 of the tube cap 120 is provided with a knurled groove 128 to facilitate increasing of friction force when the cap is manually screwed or unscrewed. An inner wall of the covering part 122 of the tube cap 120 is provided with a position-limiting rib 123, and the position-limiting rib 123 can play a role for enhancing a structural strength of the vitrification freezing carrier 100 and also play a role for position limiting when the tube cap is automatically screwed or unscrewed. An outer wall of the tube body 110 is provided with a position-limiting protrusion 119 at a position near a bottom of the vitrification freezing carrier 100 to limit the position of the tube body 110, to facilitate the locking or loosening operation to the tube cap 120.

The carrying rod 130 is arranged on a side, facing an interior of the tube body 110, of the covering part 122, that is, the carrying rod 130 can be assembled and accommodated in the tube body 110 to realize storing biological samples. The carrying rod 130A is provided with a sample placement region 132 at a position far away from the covering part 122 and adjacent to an end of the carrying rod 130A, and the sample placement region 132 is provided with a pit, and a surface of the pit is attached with an absorbent material for storing biological samples.

The auxiliary sampling mechanism 140 is configured to assist in locking the tube cap 120 to the tube body 110, or, in loosening the tube cap 120 from the tube body 110, to improve the sampling efficiency and the storage efficiency. The auxiliary sampling mechanism 140 includes a carrier body 150 and an elastic reset assembly 160. The elastic reset assembly 160 is configured to be selectively connected to the extending part 126 in a matched manner, to allow the carrier body 150 to be operated to drive the locking part 152 to move, and the movement of the locking part 152 drives the covering part 122 to move, and thus the covering part 122 can be locked to or loosened from the matching part 112, to realize closing and opening of the tube cap 120 and the tube body 110.

The carrier body 150 serves as a carrier for mounting the elastic reset assembly 160. The carrier body 150 should have a sufficient length to increase an operating distance, whereby to avoid that operation is not facilitated or hand is frostbitten due to that the tube body 110 is too short. In some embodiments, the length of the carrier body 150 is configured to be longer than the length of the tube body 110, which facilitates direct operating the carrier body 150 manually or automatically, reduces an extending distance of a manual operation or an automatic operation, and also reduces a possibility of a direct and mechanical damage to the tube cap 120 or to the tube body 110 due to a strong operating force in a manual or automatic operation.

The elastic reset assembly 160 includes the driving part 161 and the elastic part 165. The manual or automatic operation is able to drive the driving part 161 to move. Since the driving part 161 and the elastic part 165 are connected to each other, when the driving part 161 moves, it drives the elastic part 165 to move, and then the elastic part 165 is elastically deformed to realize the connecting of the elastic part 165 to the extending part 126 in a matched manner or to realize the loosening of the elastic part 165 from the extending part 126.

In some embodiments, an inner wall of the extending part 126 is provided with an engaging groove or a protrusion for accommodating and limiting a deformable portion of the elastic part 165. When the deformable portion of the elastic part 165 is accommodated and limited at the engaging groove or the protrusion, the carrier body 150 and the tube cap 120 do not separate from each other in an axial direction of the carrier body 150. In this case, the tube cap 120 can be locked to or loosened from the tube body 110 manually or automatically. When the deformable portion of the elastic part 165 is separated from the engaging groove or the protrusion, the carrier body 150 is separated from the tube cap 120. In this case, the auxiliary sampling mechanism 140 can be disassembled. For example, as shown in FIG. 3, a protrusion is provided at an opening of the extending part 126 to limit the deformable portion of the elastic part 165 and prevent the carrier body 150 from being separated from the tube cap 120.

The locking part 152 and the covering part 122 are in a detachable matching relationship, which can realize sampling and storage operations. In some embodiments, an outer wall of the covering part 122 is formed with an external threaded structure, and an inner wall of the matching part 112 is formed with an internal threaded structure. Locking the tube cap 120 to the tube body 110 or loosening the tube cap 120 from the tube body 110 can be achieved easily and reliably by utilizing the threaded matching. In this case, the locking part 152 and the covering part 122 are matched in a torque manner. It can be understood as that when the locking part 152 rotates, it can transmit torque to the covering part 122, which then drives the covering part 122 to rotate, so that the covering part 122 is screwed and locked to the matching part 112 or is unscrewed and loosened from the matching part 112. In other words, the matched connection between the locking part 152 and the covering part 122 is movable but not rotatable relative to each other in the axial direction. It should be noted that "not rotatable relative to each other" herein means that when one of the two is fixed, the other will be limited in rotating, and, when one of the two is rotated, the other will be driven to rotate.

Apparently, the locking part 152 can be completely matched with the covering part 122 in the direction of rotation, that is, as long as the locking part 152 rotates, the covering part 122 rotates correspondingly and synchronously. For example, the locking part 152 is provided with a complementary position-limiting rib which is fully matched with the position-limiting rib 123 of the covering part 122, such that the locking part 152 and the covering part 122 can rotate synchronously. The locking part 152 may also be incompletely matched with the covering part 122 in the direction of rotation, that is, the locking part 152 can be matched with the covering part 122 after rotating for a certain angle, and then drive the covering part 122 to rotate. For example, the locking part 152 is of a polygonal structure, such as a hexagonal structure, with a hexagonal cross-section, that is, there are six vertex angles in the cross-sectional view, and the position-limiting rib 123 can hinder the rotation of the six vertex angles. When the locking part 152 rotates counterclockwise or clockwise, after the locking part 152 have rotated for a certain angle, as the locking part 152 cannot overcome the resistance of the position-limiting rib 123, the locking part 152 drives the covering part 122 to rotate.

In a case where the auxiliary sampling mechanism 140 is used to assist the tube cap 120 to be locked to or loosened from the tube body 110, the locking part 152 and the covering part 122 are matched connected in torque. First, the driving part 161 is operated to cause the elastic part 165 to be elastically deformed and matched connected to the extending part 126 to prevent the locking part 152 from being separated from the covering part 122. Then, the carrier body 150 is rotated to drive the locking part 152 to rotate, and then drives the covering part 122 to rotate, so as to realize the tube cap 120 to be loosened from the tube body 110 to perform a sampling operation. Furthermore, when the elastic part 165 is matched connected to the extending part 126, the auxiliary sampling mechanism 140 may also be manually or automatically pinched to perform a positional displacement for the overall structure of the vitrification freezing carrier 100 to realize manually or automatically grabbing the overall structure of the vitrification freezing carrier 100. The auxiliary sampling mechanism 140 is used as an intermediate vehicle to avoid a mechanical damage to the tube cap 120 and the tube body 110, thereby ensuring a stable storage environment. When the elastic part 165 is no longer matched connected to the extension portion 126, since the locking part 152 and the covering part 122 can move relative to each other in the axial direction, the locking part 152 can be quickly separated from the covering part 122, and then the auxiliary sampling mechanism 140 can be disassembled quickly and conveniently, and can be applied to other freezing carrier structures, which can also have an effect of reducing the space occupied by the vitrification freezing carrier 100.

In other embodiments, the covering part 122 and the matching part 112 are connected in a non-threaded manner. An outer wall of the covering part 122 is provided with a concave portion, and an inner wall of the matching part 112 is provided with an elastic convex portion, and the locking or the loosening herein is realized through the matching between the concave portion and the elastic convex portion. For another example, the outer wall of the covering part 122 is provided with an elastic convex portion, and the inner wall of the matching part 112 is provided with a concave portion, the locking or the loosening herein is realized through the matching between the concave portion and the elastic convex portion. That is, by pressing or pulling out the covering part 122 in the axial direction, the matching between the covering part 122 and the matching part 112 is realized, and the locking of the tube cap 122 to the tube body 110 or the loosening of the tube cap 122 from the tube body 110 is then realized.

Accordingly, the locking part 152 and the covering part 122 are matched in a manner in which the locking part 152 and the covering part 122 are not movable relative to each other in the axial direction. By pressing or pulling out the carrier body 150, the locking part 152 is then pressed or pulled out, and the locking part 152 drives the covering part 122 to be locked to or loosened from the tube body 110. For example, the locking part 152 and the covering part 122 are in a concave-convex fitting manner, and the elastic part 165, while being elastically deformed, can also drive the locking part 152 to be connected to the covering part 122 in a matched manner or loosened from the covering part 122.

The above technical solutions have at least the following technical effects: the vitrification freezing carrier 100 provided by the embodiments of the present disclosure includes the tube body 110, the tube cap 120, the carrying rod 130 and the auxiliary sampling mechanism 140, and is of a tubular structure rather than of a long strip structure as a conventional freezing carrier having a thin body, so that the carrying rod 130 is protected, the structural reliability is increased, and the sealing of the structure is ensured. Compared with the conventional elongated straw, the tubular structure is not prone to being broken, which reduces the loss or damage of biological samples. Compared with the structure mainly composed of the Cryoloop, the Cryotop and the Cryoleaf, the tubular structure also reduces loss of biological samples. Utilizing the assembly relationship among the tube body 110, the tube cap 120, the carrying rod 130 and the auxiliary sampling mechanism 140, the storage of a variety of biological samples can be realized. The auxiliary sampling mechanism 140 can quickly and accurately assist in the locking of the tube cap 120 to the tube body 110 or assist in the loosening of the tube cap 120 from the tube body 110 to realize sampling and storage. It can also facilitate the automatic grabbing the overall structure of the vitrification freezing carrier 100, and reduce mechanical damage to the tube cap 120 and the tube body 110. Moreover, through the extension of the auxiliary sampling mechanism 140, a hand, to open or close the cap is prevented from being frosted by the liquid nitrogen in which the biological sample is immersed.

Figure 5:
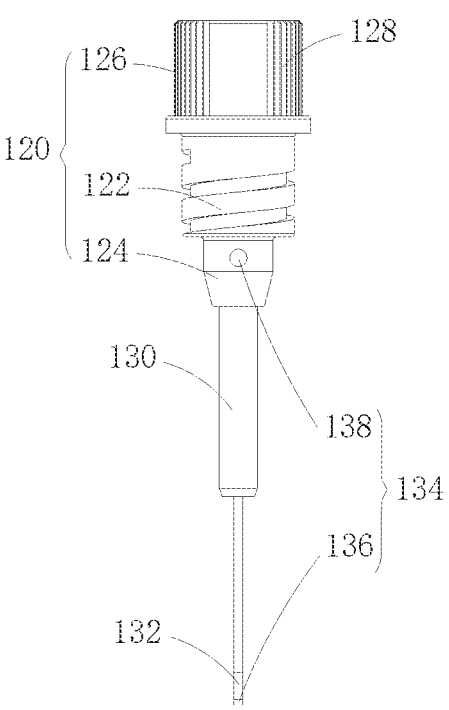
FIG. 5 is a schematic view of matching between the tube cap and the carrying rod shown in FIG. 1.
Figure 7:
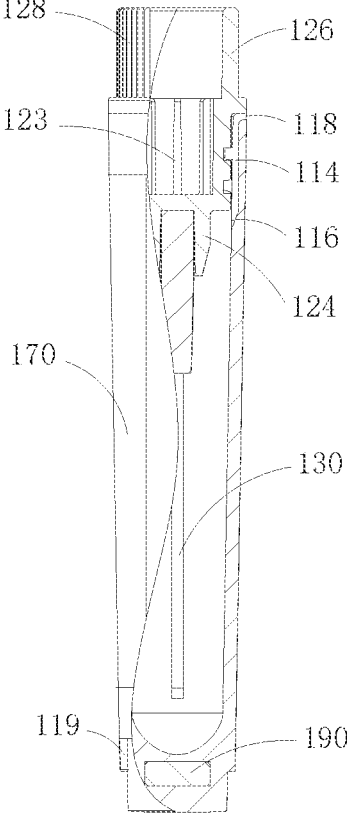
FIG. 7 is a schematic view of matching between the tube cap, the carrying rod and the tube body shown in FIG. 1 viewed in another angle.

Please continue to refer to FIGS. 3, 5, and 7. In some embodiments, the extending part 126 is of a hollow structure with two opened ends, and the extending part 126 and the covering part 122 are in connection and communication in a direction parallel to a center line of the tube body 110. The covering part 122 is substantially positioned inside the tube body 110, and the extending part 126 is positioned outside the tube body 110. In combination with the foregoing, the auxiliary sampling mechanism 140 is of a rod-shaped structure and directly extends into the extending part 126 and the covering part 122 in sequence. Apparently, in other embodiments, the extending part 126 may be provided on a side of the covering part 122, and the auxiliary sampling mechanism 140 is provided of a rod-shaped structure, which extends into the covering part 122 and is also provided of a branch-like structure, to be matched connected to the extending part 126 or loosened from the extending part 126.

Please continue to refer to FIGS. 5 to 8. In some embodiments, a mounting part 124 is provided on a side, facing the interior of the tube body 110, of the covering part 122, and the mounting part 124 is assembled with the carrying rod 130. That is, the side, where the mounting part 124 is provided, of the covering part 122 is matched with the tube body 110 to allow the carrying rod 130 to be accommodated in the tube body 110. With this arrangement, the tube cap can be matched with the carrying rods 130 used in most vitrification freezing technologies, which has a strong compatibility and reduces the costs for mold making for production and the costs for research and development. According to storage requirements, carrying rods 130 can be provided to match tube caps, to achieve diversification.

In some embodiments, the mounting part 124 may be a smooth plane, and the carrying rod 130 is connected to the smooth plane by low-temperature adhesion or ultrasonic welding. In other embodiments, the mounting part 124 may be a receiving groove, and the carrying rod 130 is partially received in the receiving groove to increase the contact area and improve the reliability of the connection. The connection of the carrying rod 130 to the mounting part 124 is also performed by low-temperature adhesion or ultrasonic welding. In other embodiments, the mounting part 124 may be an elastic clamping jaw, and the carrying rod 130 is clamped in a position-limiting space of the elastic clamping jaw. The way of assembling the mounting part 124 and the carrying rod 130 is not limited to the above-described embodiments.

Figure 4:
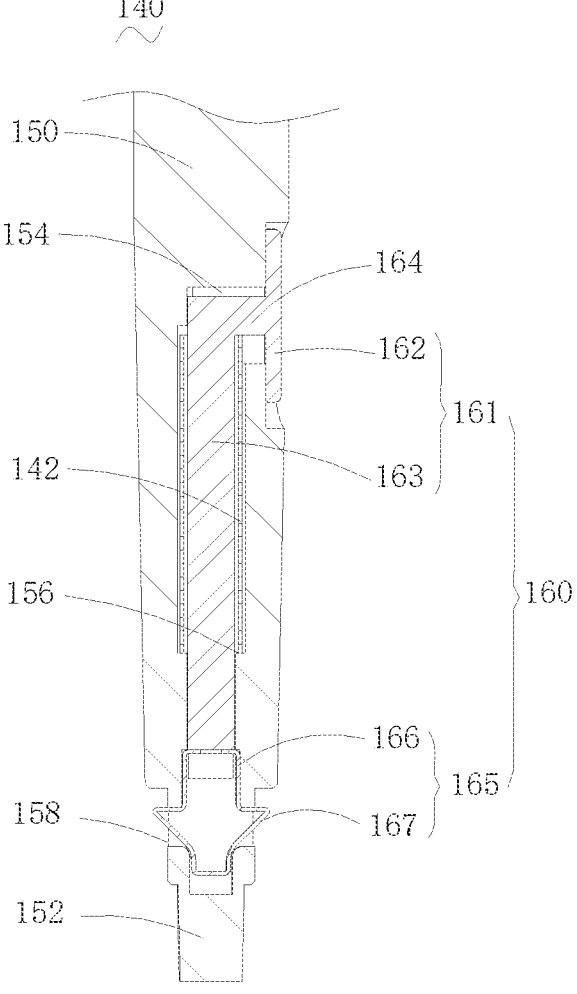
FIG. 4 is an enlarged schematic view of the auxiliary sampling mechanism shown in FIG. 3.

Please continue to refer to FIGS. 3 and 4. In some embodiments, the carrier body 150 is provided with an accommodating chamber 154, the driving part 161 is partially accommodated in the accommodating chamber 154 and partially exposed to the outside of the carrier body 150, and the elastic part 165 is accommodated in the accommodating chamber 154 and may be capable of being partially exposed to the outside of the carrier body 150. In order to reduce the space occupied by the driving part 161 and further to facilitate the operation of an operator or a manipulator, the driving part 161 is partially accommodated in the accommodating chamber 154, partially exposed to the outside of the carrier body 150, and the exposed part is used to apply an action force for generating drive. Similarly, in order to reduce the space occupied by the elastic part 165, the elastic part 165 is accommodated in the accommodating chamber 154. Since the elastic part 165 needs to be connected to the extending part 126 in a matched manner, the elastic part 165, when deformed, can be partially exposed to the outside of the carrier body 150.

Further, the driving part 161 includes a movable button 162 and a movable body 163 connected to each other. The movable button 162 is exposed to the outside of the carrier body 150 and the movable body 163 is connected to the elastic part 165 and is accommodated in the accommodating chamber 154. In this embodiment, the movable button 162 is exposed to the outside of the carrier body 150 and can be applied with an action force that drives the movable body 163 to move. The movable button 162 and the movable body 163 may be integrally formed, or may be formed by indirect locking. When the operator or manipulator pushes the movable button 162, the movable body 163 also moves as the movable button 162 and the movable body 163 are connected to each other, and the elastic part 165 also moves as the elastic part 165 and the movable body 163 are connected to each other, and further be elastically deformed, thus changing the matching connection relationship between the elastic part 165 and the extending part 126. As shown in FIG. 3, the movable button 162 can reciprocate in the axial direction of the carrier body 150, to further drive the movable body 163 to also reciprocate in the axial direction of the carrier body 150.

Furthermore, the movable body 163 is provided with a bent part 164 connected to the movable button 162, the carrier body 150 is provided with a position-limiting part 156 at the accommodating chamber 154, and a reset member 142 extending and retracting in a moving direction of the movable body 163 is provided between the bent part 164 and the position-limiting part 156. The bent part 164 and the movable button 162 are arranged with an angle of 90 degrees, and the bent part 164 enables the movable body 163 and the movable button 162 to move in a same direction and synchronously. The position-limiting part 156 may be an engaging groove, a stopper, and etc., and the reset member 142 is arranged between the bent part 164 and the position-limiting part 156, to enable the bent part 164 to automatically return after moving. The reset member 142 may be an elastic column, an elastic block, an elastic strip, and etc. that abuts against the bent part 164 and the position-limiting part 156, or the reset member 142 may be a spring sleeved on the movable body 163 and abutting against the bent part 164 and the position-limiting part 156.

Further, the carrier body 150 is provided with an opening 158 in communicating with the accommodating chamber 154. The elastic part 165 includes a fixed body 166 and a deformable body 167 that are connected to each other. The fixed body 166 is connected to the driving part 161, and the deformable body 167 is capable of extending out of the opening 158, or retracting from the opening 158. In some embodiments, the carrier body 150 is provided, at a position adjacent to the locking part 152, with an opening 158 in communication with the accommodating chamber 154. The size of the opening 158 and the shape of the opening 158 correspond to the size of the deformable body 167 and the shape of the deformable body 167. The fixed body 166 is connected to the movable body 163, and the fixed body 166 may be connected to the movable body 163 in a position-limiting manner by means of bonding, buckling, or a position-limiting groove, to allow the movable body 163 to drive the fixed body 166 to move. The fixed body 166 and the deformable body 167 may be integrally formed or formed by indirect locking. The fixed body 166 and the deformable body 167 are made from elastic materials.

When the movable button 162, the movable body 163, and the deformable body 167 are in an initial state, the movable button 162 and the movable body 163 are located relatively far away from the locking part 152 under the action of the reset member 142, and the deformable body 167 extends out from the opening 158 and connected to the inner wall of the extending part 126 in a matched manner. When the movable button 162 drives the movable body 163 to move toward to the locking part 152, the movable body 163 drives the fixed body 166 to move synchronously, and the fixed body 166 drives the deformable body 167 to move. Since the deformable body 167 is constrained by the opening 158, the deformable body 167 deforms and retracts from the opening 158. In this case, the auxiliary sampling mechanism 140 may be disassembled.

For example, referring to the placement postures shown in FIG. 3 and FIG. 4, the fixed body 166 and the deformable body 167 are integrally formed spring piece, and the spring piece is provided with sharp corners that can extend out from the opening 158, and the reset member 142 is a spring sleeved on the movable body 163. When the tube body 110 is needed to be placed in a liquid nitrogen for being frozen, the movable button 162 is pushed down, and the movable button 162 drives the bent part 164 to press the spring, and drives the movable body 163 to move downward synchronously, so that the spring piece moves downward, and the spring piece is deformed, with its two sharp corners retracting, so that the locking part 152 is inserted into the covering part 122. Then the movable button 162 is released, and the movable button 162 is reset under the action of the spring, and then the spring piece is deformed, with its two sharp corners protruding, to be connected to the inner wall of the extending part 126 in a matched manner. In this case, the locking part 152 is matched with the covering part 122 to lock the tube cap 120 to the tube body 110, and the auxiliary sampling mechanism 140 is operated manually or automatically, to place the tube body 110 into the liquid Nitrogen environment. When sampling is required, the carrier body 150 is manually or automatically operated to drive the locking part 152 to move, and the locking part 152 drives the covering part 122 to move to realize the cap opening operation. When the auxiliary sampling mechanism 140 is to be disassembled, the movable button 162 is pushed again, to separate the carrier body 150 from the tube cap 120 while the two sharp corners retract. For another example, the deformable body 167 may be an elastic block, and in this case, when a pushing force is received, the deformable body 167 may be elastically deformed and retract from the opening 158 due to the restriction of the opening 158, and when the pushing force is cancelled, the deformable body 167 may be elastically restored and extend out from the opening 158.

Please continue to refer to FIG. 7. In some embodiments, the tube body 110 is provided with a gas discharge passage 114 which allows an inside of the tube body 110 to be in communication with an outside of the tube body 110. The gas discharge passage 114 is embedded in the matching part 112, and the gas discharge passage 114 is provided with an inlet end 116 and an outlet end 118. The inlet end 116 is provided on a side, away from the extending part 126, of the matching part 112 and faces the inside of the tube body 110, and the outlet end 118 is provided on a side, close to the extending part 126, of the matching part 112 and faces the outside of the tube body 110. The gas discharge passage 114 is embedded in the matching part 112 to avoid adversely affecting the accuracy and reliability of matching the matching part 112 with the covering part 122, and avoid interfering the matching relationship between the matching part 112 and the covering part 122 physically. That is, in a case where an internally threaded structure is provided in the inner wall of the matching part 112, the internally threaded structure still maintains a complete shape uninterrupted, and the gas discharge passage 114 passes through a tube wall where the matching part 112 is provided. The inlet end 116 is provided on the side, away from the extending part 126, of the matching part 112, that is, a side not adversely affecting a starting end of the matching relationship between the matching part 112 and the covering part 122, and the outlet end 118 is provided on the side, adjacent to the extending part 126, of the matching part 112, that is, a side not adversely affecting a terminal end of the matching relationship between the matching part 112 and the covering part 122. With such arrangements, the gas discharge passage is arranged with a certain tortuous path, which can prevent foreign matter from falling into the tube body 110 and reduce possibility of contamination of biological samples. The gas discharge passage 114 can prevent a tube burst phenomenon caused by volatilization of liquid nitrogen in the tube body 110, and promptly discharge the gas volatilized from the liquid nitrogen out of the tube body 110.

Figure 8:
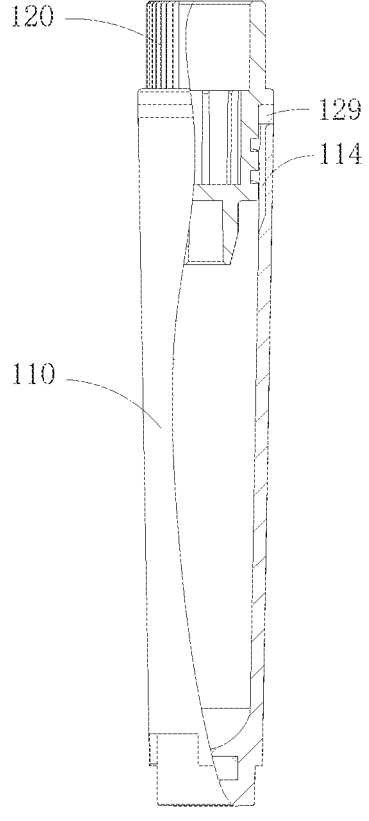
FIG. 8 is a schematic view of matching between a tube cap and a tube body according to another embodiment of the present disclosure.
Figure 9:
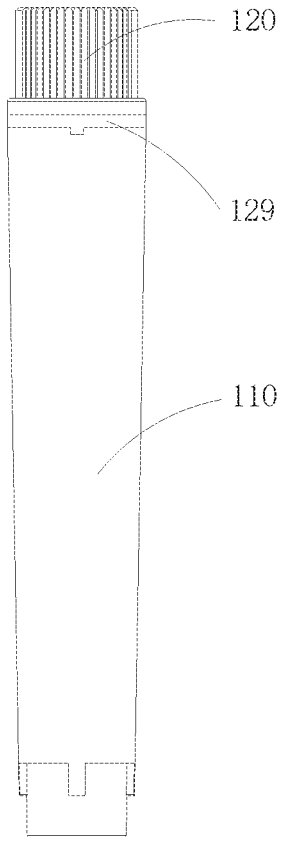
FIG. 9 is a schematic view of an appearance of the tube cap and the tube body shown in FIG. 8.

Please continue to refer to FIG. 8 and FIG. 9. Further, since biological samples include different types of samples such as cells, embryos, tissues, organs, and etc., when an airtight environment is strictly required, a sealing ring 129 is additionally provided to an outer side of the tube cap 120 to seal the outlet end 118 of the gas discharge passage 114, so that the tube body 110 is formed as a sealed chamber. In this case, due to the size of the storage space, the carrying rod 130 may also be directly removed, and the biological sample may be directly placed in the tube body 110.

Please continue to refer to FIG. 7. In some embodiments, a two-dimensional code 170 is provided on a side of the tube body 110 and/or a bottom of the tube body 110. The two-dimensional code 170 may be provided by laser engraving, so that it has good abrasion resistance and can maintain the clarity of the two-dimensional code 170 even after being repeatedly used for many times. In order for the stored information of different biological samples to be replaceable, the two-dimensional code 170 may also be pasted so as to be replaced in a timely manner. Apparently, when the storage information requirements are low, a one-dimensional code or a barcode may be used instead of the two-dimensional code 170. For example, a two-dimensional code 170 is provided on the bottom of the tube body 110, and a one-dimensional code is provided on the side of the tube body 110. The two-dimensional code 170 can facilitate intelligent identification for an automated system, and thus an automated matching operation can be realized. When the automated system may collect biological samples and establish a biological sample library while performing intelligent identification, which facilitates sample traceability and data management.

Figure 6:
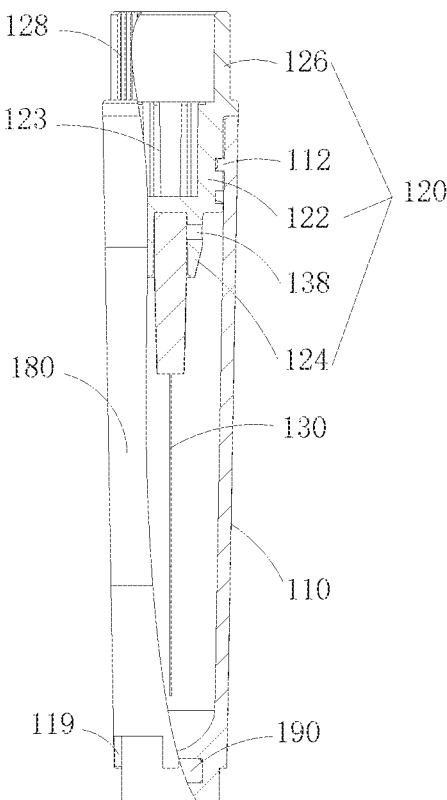
FIG. 6 is a schematic view of fitting between the tube cap, the carrying rod and a tube body shown in FIG. 1.

Please continue to refer to FIG. 6, in some embodiments, the side of the tube body 110 is provided with a writing region 180, and the carrying rod 130 is provided with an indication region 134, and a projection of the indication region 134 on the tube body 110 is located at a position other than the writing region 180. In this embodiment, the projection of the indication region 134 on the tube body 110 is also located at a position other than the two-dimensional code 170. The writing region 180 can facilitate making information remarks for the biological samples by an operator, and play a role of reminding and warning for subsequent operations. In a case where the two-dimensional code 170 cannot identify specific information, the writing region 180 is used to assist the identification, thereby providing a dual identification. In order to prevent the writing region 180 from adversely affecting the observation of the indication region 134, the indication region 134 and the writing region 180 are arranged separately, that is, the projection of the indication region 134 and the projection of the writing region 180 on the tube body 110 do not overlap.

Please continue to refer to FIG. 5. Further, the indication region 134 includes an identification mark 136 arranged adjacent to the sample placement region 132. The identification mark 136 may be a color indicator point or an indicator block with a concave-convex structure to clearly indicate the location of the sample placement region 132, and to facilitate quickly and accurately identifying biological samples. The indication region 134 further includes a round hole mark 138, or a color indicator point, or a concave-convex indicator block, and etc., which is arranged on the carrying rod 130 adjacent to the mounting part 124 or directly arranged on the mounting part 124 to indicate a placement surface of the sample placement region 132. Arranged as such, the biological samples can be found out in a short time, the operation time can be reduced, and the damage to the biological samples can be reduced.

In some embodiments, the tube cap 120 is of different colors to distinguish types, quality levels, or particularities of the biological samples. Different biological samples may be distinguished by using tube caps 120 of different colors, so that intelligent or manual identification can be quickly performed, and the operation can be speeded up, and the quality of the operation can be improved.

Please continue to refer to FIGS. 6 to 8. In some embodiments, a counterweight 190 is embedded in a bottom of the tube body 110, and a center line of the counterweight 190 coincides with the center line of the tube body 110. In this embodiment, the center line refers to a center line in an extension length direction of the tube body 110. The bottom of the tube body 110 has a certain wall thickness, which provides sufficient space for the counterweight 190 to ensure that the counterweight 190 can be embedded in the bottom. In some embodiments, the bottom of the tube body 110 may be provided with a recess, and is then sealed after the counterweight 190 is embedded. In other embodiments, in the process of preparing the tube body 110 by injection molding, the counterweight 190, is integrally formed with the tube body 110 as an embedded member during the injection molding process. The counterweight 190 is made from non-heavy metal materials, such as aluminum, stainless steel, and etc., to prevent the biological sample from being adversely affected and losing activity. The counterweight 190 can prevent the tube body 110 from floating in the liquid, and ensure that the tube body 110 can be placed vertically by its own gravity, thereby reducing the possibility of damaging the biological sample due to the positional deviation of the tube body 110, and improving the viability and development ability of the biological samples which are resuscitated after frozen. The center line of the counterweight 190 coincides with the center line of the tube body 110, which can further ensure that the tube body 110 can be placed vertically by its own gravity. For example, the counterweight 190 may adopt a cylindrical structure with a circular cross section perpendicular to the center line of the tube body 110. The counterweight 190 may also adopt a regular polygon structure whose cross section perpendicular to the center line direction of the tube body 110 is a regular polygon.

The technical features of the above embodiments can be combined arbitrarily. To make the description concise, not all possible combinations of the technical features in the above embodiments are described. However, as long as there is no contradiction in the combinations of these technical features, those combinations should be construed as falling into the range set forth in this specification.

The above examples only express a few embodiments of the present invention, and their descriptions are relatively specific and detailed, but those examples should not be understood as a limitation on the scope of the invention patent. It is to be noted that for those of ordinary skill in the art, several modifications and improvements can be made without departing from the concept of the present invention, and all of these fall within the protection scope of the present invention. Therefore, the protection scope of the present invention patent is defined by the appended claims.

What is claimed is:

1. A vitrification freezing carrier, comprising:
a tube body, wherein the tube body is of a hollow structure with an opened end, and a matching part is provided at the opened end;
a tube cap, wherein the tube cap is provided with a covering part and an extending part, the covering part matches the matching part, the extending part is connected to the covering part, and the covering part is of a hollow structure with one end closed;
a carrying rod, wherein the carrying rod is arranged on a side, facing an interior of the tube body, of the covering part, and the carrying rod extends into the tube body when the tube cap is attached to the tube body and is removable from the tube body when the tube cap is separated from the tube body; and
an auxiliary sampling mechanism, wherein the auxiliary sampling mechanism comprises a carrier body and an elastic reset assembly arranged on the carrier body, the carrier body is provided with a locking part, the locking part is configured to be matched with the covering part to drive the covering part to move, the elastic reset assembly comprises a driving part and an elastic part driven by the driving part, the elastic part is movable from a first position to a second position, in the first position, the elastic part is connected to the extending part in a matched manner, and in the second position, the elastic part is detached from the extending part, and an inner wall of the extending part is used to limit the elastic part from detaching from the extending part;
wherein the carrier body is provided with an accommodating chamber, the driving part is partially accommodated in the accommodating chamber and partially exposed to an outside of the carrier body, and the elastic part is accommodated in the accommodating chamber and is partially exposed to the outside of the carrier body when in the first position;
wherein the carrier body is provided with an opening in communication with the accommodating chamber, the elastic part comprises a fixed body and a deformable body which are connected to each other, the fixed body is connected to the driving part, and the deformable body extends out of the opening when the elastic part is in the first position and is retracted from the opening when the elastic part is in the second position, and in response to the deformable body being extended out from the opening in the first position, the deformable body is elastically deformed and connected to the inner wall of the extending part.

2. The vitrification freezing carrier according to claim 1, wherein the extending part is of a hollow structure with two opened ends, and the extending part and the covering part are in connection and communication with each other in a direction parallel to a center line of the tube body.

3. The vitrification freezing carrier according to claim 1, wherein a mounting part is provided on the side, facing the interior of the tube body, of the covering part, and the mounting part is assembled with the carrying rod.

4. The vitrification freezing carrier according to claim 1, wherein the driving part comprises a movable button and a movable body which are connected to each other, the movable button is exposed to the outside of the carrier body, and the movable body is connected to the elastic part and accommodated in the accommodating chamber.

5. The vitrification freezing carrier according to claim 4, wherein the movable body is provided with a bent part connected to the movable button, the carrier body is provided with a position-limiting part at the accommodating chamber, and a reset member extending and retracting in a moving direction of the movable body is provided between the bent part and the position-limiting part.

6. The vitrification freezing carrier according to claim 1, wherein the tube body is provided with a gas discharge passage which allows an inside of the tube body to be in communication with an outside of the tube body, the gas discharge passage is embedded in the matching part, the gas discharge passage is provided with an inlet end and an outlet end, the inlet end is arranged on a side, away from the extending part, of the matching part and faces the inside of the tube body, and the outlet end is arranged on a side, close to the extending part, of the matching part and faces the outside of the tube body.

7. The vitrification freezing carrier according to claim 1, wherein a two-dimensional code is provided on the tube body.

8. The vitrification freezing carrier according to claim 1, wherein a counterweight is embedded in a bottom of the tube body, and a center line of the counterweight coincides with a center line of the tube body.

9. The vitrification freezing carrier according to claim 6, wherein a sealing ring is additionally provided to an outer side of the tube cap to seal the outlet end of the gas discharge passage.

10. The vitrification freezing carrier according to claim 7, wherein a side of the tube body is provided with a writing region, and the carrying rod is provided with an indication region.

11. The vitrification freezing carrier according to claim 10, wherein a projection of the indication region on the tube body is located at a position other than the writing region, and the projection of the indication region on the tube body is located at a position other than the two-dimensional code.

12. The vitrification freezing carrier according to claim 7, wherein the two-dimensional code is provided on the bottom of the tube body, and a one-dimensional code is provided on the side of the tube body.

13. Two or more vitrification freezing carriers according to claim 1, wherein the two or more vitrification freezing carriers have differently colored tube caps.

14. The vitrification freezing carrier according to claim 8, wherein the counterweight is integrally formed with the tube body.

* * * * *